(12) United States Patent
Ettinger

(10) Patent No.: US 9,134,288 B1
(45) Date of Patent: Sep. 15, 2015

(54) MULTIMODE DIAL INDICATOR FOR PERISHABLE FOODSTUFF

(71) Applicant: Kerry R. Ettinger, San Rafael, CA (US)

(72) Inventor: Kerry R. Ettinger, San Rafael, CA (US)

( * ) Notice: Subject to any disclaimer, the term of this patent is extended or adjusted under 35 U.S.C. 154(b) by 455 days.

(21) Appl. No.: 13/708,821

(22) Filed: Dec. 7, 2012

Related U.S. Application Data

(60) Provisional application No. 61/570,085, filed on Dec. 13, 2011.

(51) Int. Cl.
*G09F 11/23* (2006.01)
*A61J 7/04* (2006.01)
*G01N 33/04* (2006.01)

(52) U.S. Cl.
CPC ..................... *G01N 33/04* (2013.01)

(58) Field of Classification Search
CPC ............... A61J 7/04; A61J 9/00; G09F 11/23; G01N 33/04
USPC ......... 116/308, 309, 310, 311, 312, 313, 315, 116/316, 317, 318, 319; 40/310, 311, 665; 206/459.1; 215/11.1, 230, 365; 374/150; D9/547; D10/46.2
See application file for complete search history.

(56) References Cited

U.S. PATENT DOCUMENTS

| | | | | |
|---|---|---|---|---|
| 576,834 | A * | 2/1897 | Chapman | 116/308 |
| 727,645 | A * | 5/1903 | Lea | 116/308 |
| 1,796,398 | A * | 3/1931 | Richardson | 116/308 |
| 2,976,629 | A * | 3/1961 | Lubis et al. | 40/310 |
| D206,106 | S | 10/1966 | Murray et al. | |
| 3,852,900 | A * | 12/1974 | Svec | 40/495 |
| 4,224,894 | A * | 9/1980 | Haldemann | 116/209 |
| 4,345,541 | A | 8/1982 | Villa-Real | |
| D309,902 | S | 8/1990 | Schneider | |
| 5,020,468 | A * | 6/1991 | Ciminelli | 116/318 |
| 5,577,335 | A | 11/1996 | Tucker | |
| 6,152,067 | A | 11/2000 | Mathison | |
| D481,946 | S | 11/2003 | Nicholson et al. | |
| 6,802,279 | B1 * | 10/2004 | Johnson | 116/306 |
| 6,805,072 | B1 * | 10/2004 | DeSano | 116/308 |
| 6,857,935 | B1 | 2/2005 | Dohan | |
| 7,061,832 | B1 | 6/2006 | Lansing | |
| D532,827 | S | 11/2006 | Garfinkle | |
| D556,606 | S | 12/2007 | Stauffer et al. | |
| 7,472,797 | B2 | 1/2009 | Ostrowski | |
| 7,555,995 | B1 * | 7/2009 | Stump et al. | 116/311 |
| 7,661,384 | B2 | 2/2010 | Mataya | |
| 7,742,360 | B1 * | 6/2010 | Price | 368/10 |
| 8,020,507 | B2 | 9/2011 | Strong | |

(Continued)

FOREIGN PATENT DOCUMENTS

GB 2479387 A * 10/2011 ............ G09F 11/04

OTHER PUBLICATIONS

Baby Chef Formula Freshminder, FAO Schwarz, Aug. 2010.

*Primary Examiner* — Richard A. Smith
(74) *Attorney, Agent, or Firm* — Patent Law Offices of Michael E. Woods; Michael E. Woods

(57) ABSTRACT

A freshness system including an indicator disposed on a storage bottle. The indicator enables a caregiver to identify when a volume breast milk was pumped/expires when the storage bottle includes breast milk; and to identify when a certain amount of formula was prepared/expires when the storage bottle includes formula; and to distinguish between the breast milk container and the formula container.

14 Claims, 15 Drawing Sheets

(56) References Cited

U.S. PATENT DOCUMENTS

| | | |
|---|---|---|
| D681,490 S | 5/2013 | Stansbury et al. |
| 8,441,893 B2 | 5/2013 | Stephens Stauffer et al. |
| 8,590,185 B1 | 11/2013 | Jardine |
| D704,266 S * | 5/2014 | Ettinger .................. D20/18 |
| 2004/0205989 A1 | 10/2004 | Michaels |
| 2004/0257918 A1 | 12/2004 | Ribi |
| 2006/0062085 A1 | 3/2006 | Evans |
| 2006/0181961 A1 | 8/2006 | Hobkirk |
| 2008/0279724 A1 | 11/2008 | Dicarlo |
| 2009/0025625 A1 | 1/2009 | Lee |
| 2009/0084305 A1 | 4/2009 | Song |
| 2013/0062346 A1 | 3/2013 | Killinger et al. |

* cited by examiner

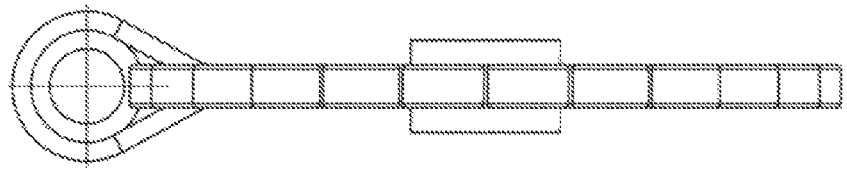
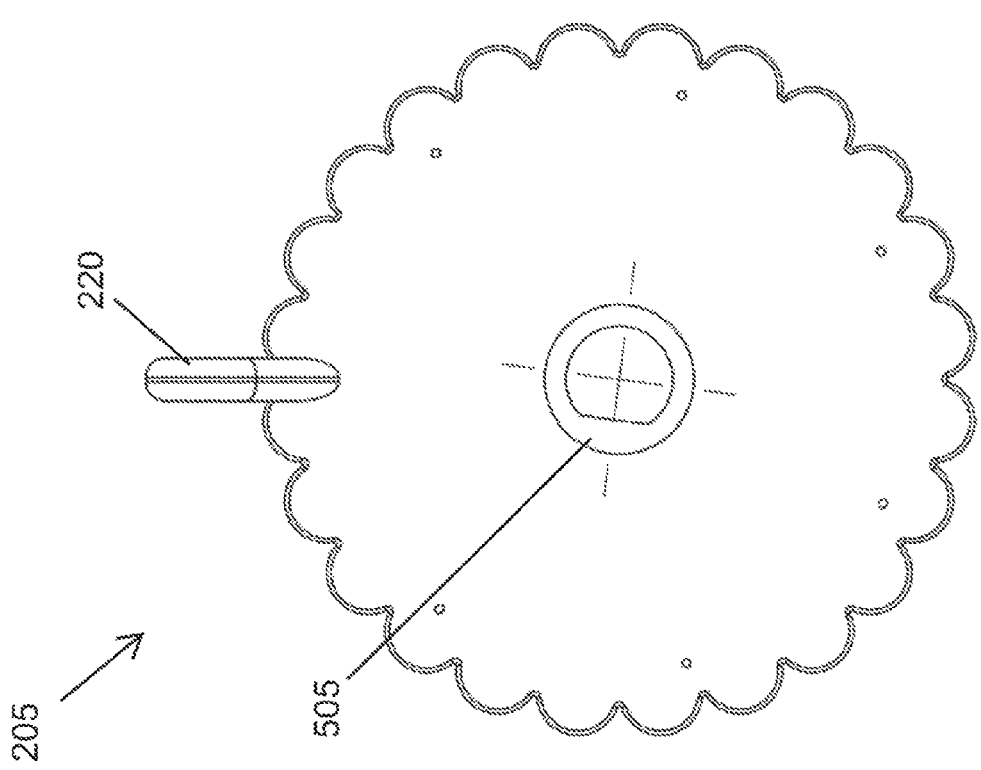
FIG. 6
FIG. 5

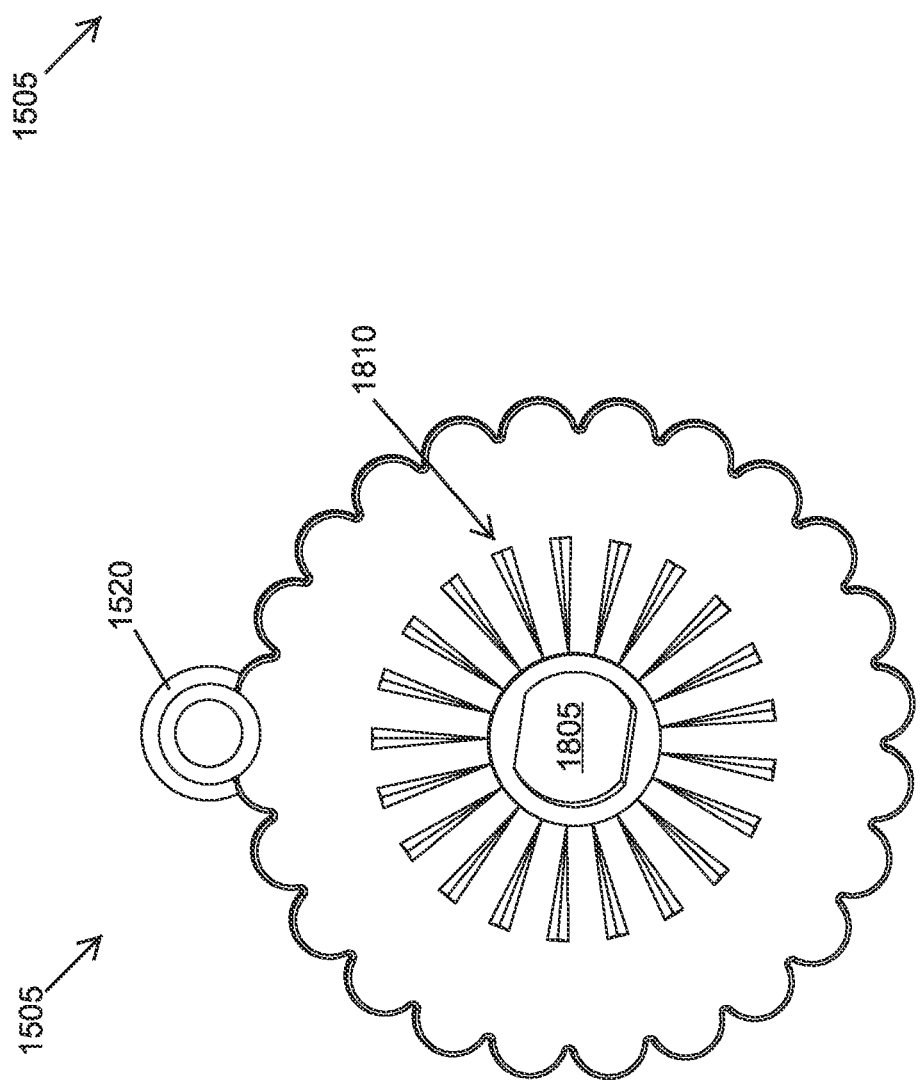

MULTIMODE DIAL INDICATOR FOR PERISHABLE FOODSTUFF

CROSS REFERENCE TO RELATED APPLICATIONS

This application claims the benefit of U.S. Provisional Application No. 61/570,085, filed 13 Dec. 2011, the contents of which are expressly incorporated in its entirety for all purposes.

BACKGROUND OF THE INVENTION

The present invention relates generally to a freshness indicator for containers of perishable foodstuff, and more particularly but not exclusively, to an indicator associable with a bottle containing infant fluid nutrition that visualizes important information concerning the bottle contents.

For purposes of this application, fluid nutrition for infants is categorized into two classes: breast milk and formula. These categories are not always easily differentiated when disposed in a container, particularly when a caregiver is moving quickly to make preparations for feeding the infant. It is the case that these products are often disposed in identical baby bottles, side-by-side on a refrigerator shelf. Each product has specifics as to freshness and shelf-life, and it is important for a caregiver to be able to quickly, confidently, and unambiguously make a correct decision for which type of product to be fed to the infant, as well as avoiding products that exceed freshness criteria.

With respect to breast milk, it is important that the caregiver be able to determine when the breast milk was pumped/expires which is important when gauging a proper time for feeding, refrigerating, and/or freezing the breast milk. This is also true for formula: that the caregiver be able to determine when the formula was prepared in order to gauge a proper time for feeding, refrigerating, and/or discarding it.

Efficient organization of fluid nutrition is important to minimize waste, free valuable time for the caregiver for more important tasks, and reduce possible confusion over care and feeding of the infant. A challenge to conventional organization solutions is that there is no universal solution for storing and delivering infant fluid nutrition having visually similar classes, with each class having a different freshness expiration metric. There are different delivery systems (e.g., baby bottles), many of which also serve as storage devices.

No single conventional add-on product easily identifies when a volume of breast milk was pumped/expires, identifies when a particular quantity of formula was prepared, and distinguishes between the two categories of products stored for use in a refrigerator while being universally applicable to any type of delivery and/or storage solution.

Conventional organizational systems include: (1) sticky notes; (2) masking tape/label; (3) direct marking with grease pencil or the like; (4) independent electronic timers; and (5) other systems, including electronic timers, which are integrated into a bottle. These systems have drawbacks that can be improved upon to enable a single universal solution. The drawbacks include smudging, deposit of hard-to-remove residues, propensity for disassociation with the bottle, specialization for one of the fluid nutrition systems, and/or inability to be adapted to a caregiver's choice of fluid delivery system.

What is needed is an apparatus and method for a single universal solution for a freshness indicator of infant fluid nutrition disposed within a delivery and/or storage system.

BRIEF SUMMARY OF THE INVENTION

Disclosed is an apparatus and method for a single universal solution for a freshness indicator of infant fluid nutrition disposed within a delivery and/or storage system. The present invention includes embodiments directed towards a single device/method that identifies when a volume breast milk was pumped/expires that is compatible with any type of bottle; and identifies when a certain amount of formula was prepared/expires; and distinguishes between the two when both are stored side-by-side (breast milk and formula have a very similar appearance and can easily be confused). Similar appearance means a closely matching color having similar light transmission and opacity characteristics.

A freshness system indicating an expiration of a fluid nutrition in a container, including a planar base having a first side and a second side, the first side including a first freshness scheme and associated first plurality of freshness indicia and the second side including a second freshness scheme and associated second plurality of freshness indicia; a first dial rotatably coupled to the first side having a first rotation mode, the first dial including a first pointer and the first rotation mode associating the first pointer with a particular one indicia of the first plurality of indicia; a second dial rotatably coupled to the second side having a second rotation mode, the second rotation mode independent from the first rotation mode, the second dial including a second pointer and the second rotation mode associating the second pointer with a particular one indicia of the second plurality of indicia; and an attachment system, selectively and removably associating the planar base to the container with a particular one of the first side or the second side substantially visible and the second side substantially obscured, wherein the pointer of the particular one side that is visible visibly identifies the expiration of the fluid within the container by reference to the associated particular one indicia.

A method indicating an expiration of a fluid nutrition in a container, including a) determining the expiration of the fluid nutrition; b) setting one independent pointer of a plurality of independent pointers visually identifying the expiration from a set of candidate expirations associated with each independent pointer, each pointer associated with an independent freshness scheme having appropriate associated indicia and each freshness scheme providing a different set of candidate expirations; and c) associating removably the one independent pointer to an outside of the container with the one independent pointer visible from a visual examination of the independent pointer without contacting or moving the one independent pointer.

A freshness indicating system removably associative with a container of infant nutrition, the infant nutrition having an infant nutrition freshness expiration, including: a customizable variable indicator having a first mode and a second mode, each mode associated with a different freshness expiration scale having an independently interacting indicator selecting a particular freshness expiration from a set of freshness expirations; and an engagement system, coupled to the customizable variable indicator, selectively and repeatably associative with the container presenting a particular one mode of the modes on an exterior of the container for visual external inspection of the associated freshness expiration scale with the particular one mode including the independently interacting indicator selecting the infant nutrition freshness expiration.

One of the advantages of the disclosed embodiments is that the structures enable a caregiver to track, using a single associative indicator, either an expiration day or an expiration time, of infant nutrition stored in a container, appropriate for the class of infant nutrition and/or the freshness expiration range. In some embodiments, the indicator supports multiple operational modes and each mode has a freshness range appropriate for one class of a plurality of different classes of infant nutrition. In some situations, storage conditions may move a class of infant nutrition from one range normally associated with its class to another freshness range associated with another class. There are embodiments which enable the freshness indicator to indicate the appropriate freshness range in such cases.

In the disclosed embodiments, an associated indicator has one of a plurality independent indication mechanisms, one of which is externally visible at any time when associated with a container. The container may be virtually any type of container used in the context of infant nutrition. Some of the embodiments include a transparent bottle enabling the caregiver to see the fluid infant nutrition within. The fluid infant nutrition can be one of two classes—breast milk or formula. That visible independent indication mechanism is chosen to do at least one (and in some cases, both) of these functions: provide the expiration, provide an indication of class, or both. This indication mechanism is not integrated into the container, but is modular and is adapted to be associable with virtually any container.

Features/benefits include assisting caregivers to easily organize and keep track of pumped/expired breast milk and/or prepared formula to minimize waste, minimize time needed to organize stock, and minimize confusion over which bottle to feed the baby. This is especially useful when sleep deprivation is high and when there are other competing demands for the caregiver's attention.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1-FIG. 13 illustrate a first freshness system and FIG. 14-FIG. 26 illustrate an alternative freshness system;

FIG. 1 illustrates a perspective view of the first freshness system including an indicator disposed on a storage bottle;

FIG. 2 illustrates a front plan view of the indicator shown in FIG. 1;

FIG. 3 illustrates a sectional view of the indicator;

FIG. 4 illustrates a side view of the indicator;

FIG. 5 illustrates a front view of a base for the indicator;

FIG. 6 illustrates a side view of the base;

FIG. 7 illustrates a front view of a dial for the indicator;

FIG. 8 illustrates a side view of the dial;

FIG. 9 illustrates a front view of a first half of a coupler for the indicator;

FIG. 10 illustrates a side view of the first half of the coupler;

FIG. 11 illustrates a side view of a second half of the coupler for the indicator;

FIG. 12 illustrates a front view for the second half of the coupler;

FIG. 13 illustrates a sectional view of the second half of the coupler.

FIG. 14 illustrates a perspective view of the alternative freshness system including an indicator disposed on a storage bottle;

FIG. 15 illustrates a front plan view of the indicator shown in FIG. 14;

FIG. 16 illustrates a sectional side view of the indicator shown in FIG. 14;

FIG. 17 illustrates a side view of the indicator shown in FIG. 14;

FIG. 18 illustrates a front view of a base for the indicator shown in FIG. 14;

FIG. 19 illustrates a side view of the base shown in FIG. 14;

FIG. 20 illustrates a front view of a dial for the indicator shown in FIG. 14;

FIG. 21 illustrates a side view of the dial shown in FIG. 14;

FIG. 22 illustrates a front view of a first half of a coupler for the indicator shown in FIG. 14;

FIG. 23 illustrates a sectional side view of the first half of the coupler shown in FIG. 22;

FIG. 24 illustrates a first side of the indicator shown in FIG. 14 with a first representative freshness scale;

FIG. 25 illustrates a second side of the indicator shown in FIG. 14 with a second representative freshness scale; and FIG. 26 illustrates a functional sectional view side view of the indicator shown in FIG. 14.

DETAILED DESCRIPTION OF THE INVENTION

Embodiments of the present invention provide an apparatus and method for a single universal solution for a freshness indicator of infant fluid nutrition disposed within a delivery and/or storage system. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

In some systems, a freshness indicator is sometimes used interchangeably with tamper-evidence seals or indicators. The present invention does not use freshness indicator in this fashion. Freshness indication in the context of the present invention relates to a short-hand reference to a shelf life of different classes of fluid infant nutrition as influenced by the refrigeration/storage state.

Figure 1:
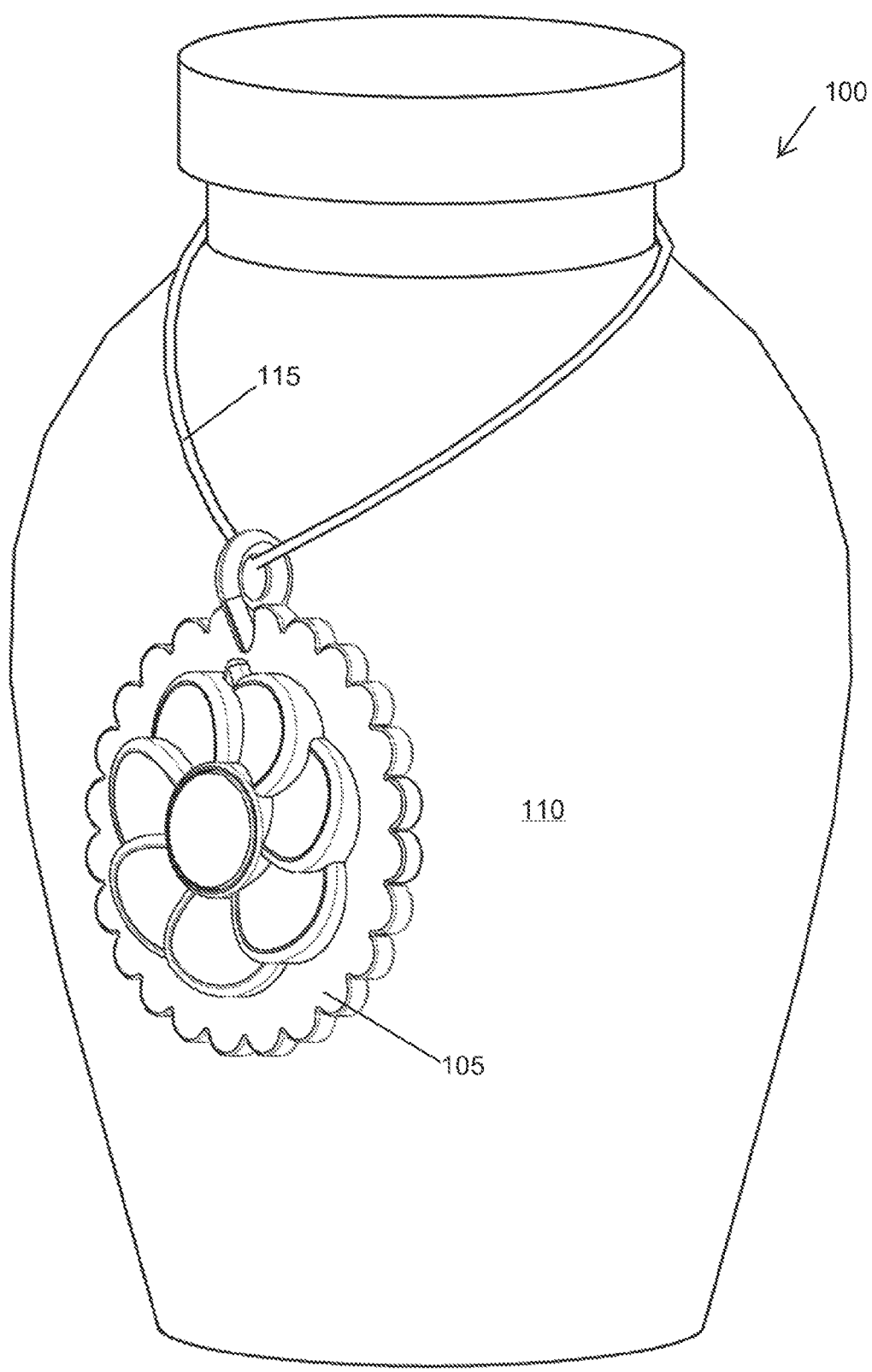

FIG. 1 illustrates a perspective view of a freshness system 100 including an indicator 105 disposed on a storage bottle 110. Indicator 105 enables a caregiver to identify when a volume breast milk was pumped/expires when storage bottle 110 includes breast milk; and to identify when a certain amount of formula was prepared/expires when storage bottle 110 includes formula; and to distinguish between the breast milk and formula. Indicator 105 is two-sided, each side associated with one of the categories of infant fluid nutrition that may be contained within storage bottle 110. The association is performed by indicia, label, color, pattern, or other feature or device that enables quick and easy differentiation. In the preferred embodiment, it is advantageous that a caregiver be able to quickly determine, by reviewing which side of indicator 105 is facing outward, whether storage bottle 110 includes breast milk or formula.

In addition, each side includes a dial that is used to indicate freshness for the particular type of infant fluid nutrition contained within. These dials are independently operable and changing one dial on one side does not change the other dial on the other side. The specific freshness indication of each dial is customized for the associated category. For example, many caregivers believe it is important to know which day a volume of breast milk was pumped/expires. Therefore for this implementation, the side of indicator 105 associated with breast milk has day indicia disposed thereon. Similarly, many caregivers believe it is important to know what hour a volume of formula was prepared. The side of indicator 105 associated with formula has hour indicia disposed thereon. The caregiver is thus easily to use indicator 105 to differentiate between a type of infant fluid nutrition disposed within storage bottle 110, but to also indicate the appropriate freshness metric for the specific category. By using a universal attachment system, e.g., an elastomeric loop 115 coupled to indicator 105, indicator 105 may be used with virtually any size, style, or other configuration of fluid delivery system.

Figure 2:
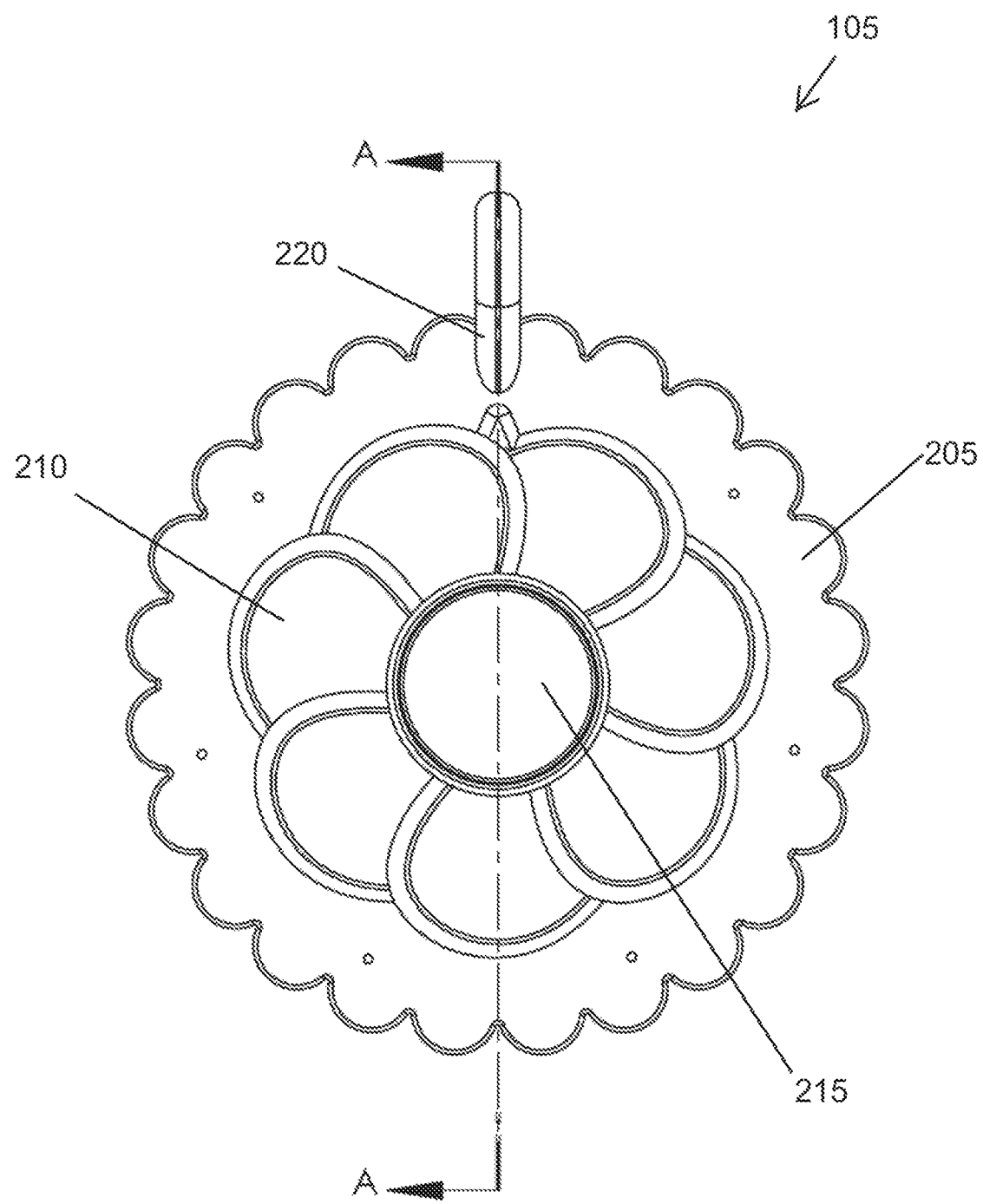
Figure 3:
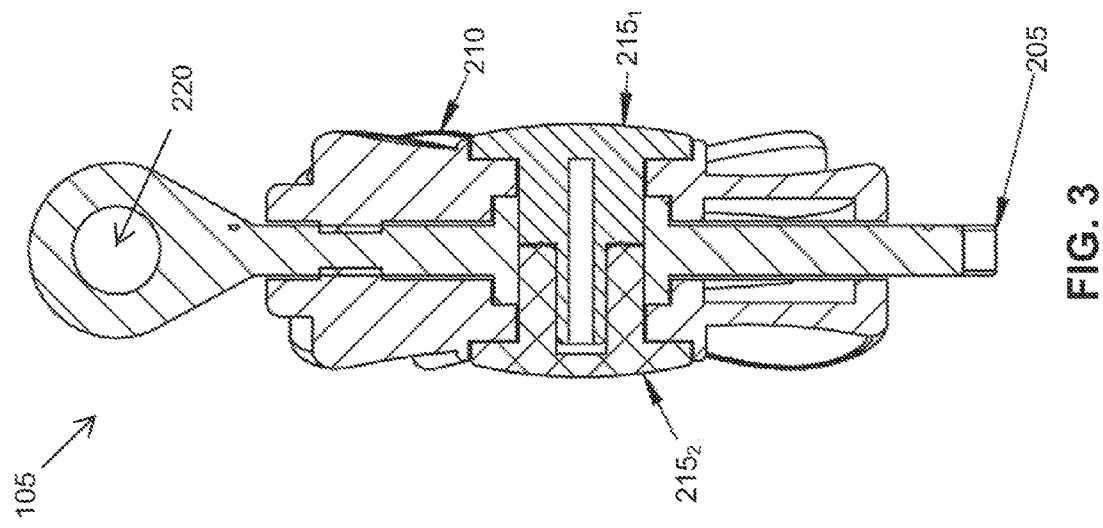
Figure 4:
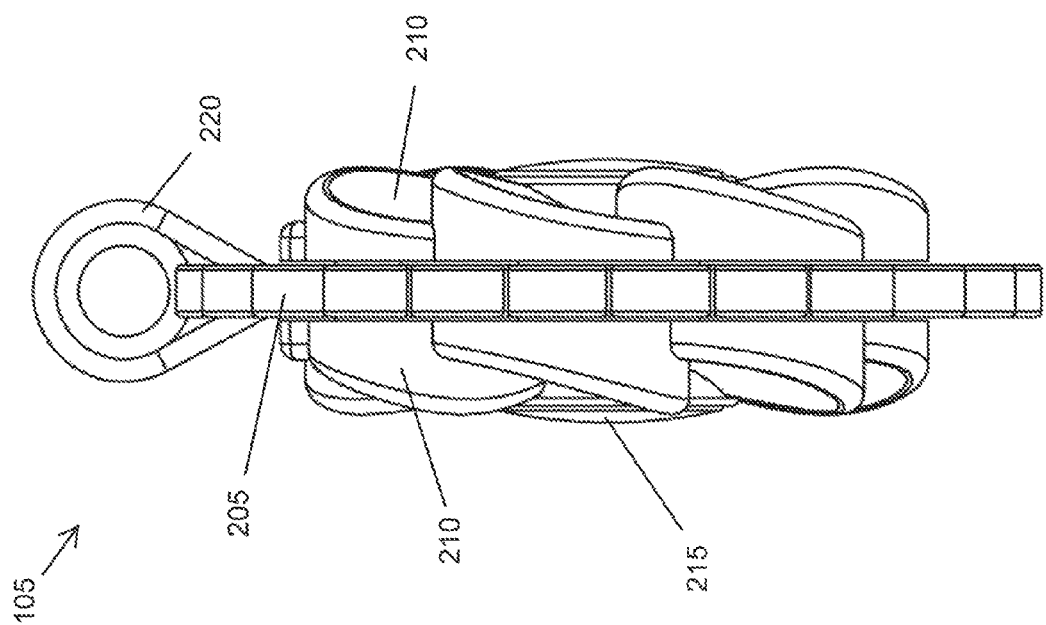

FIG. 2 illustrates a front plan view of indicator 105 shown in FIG. 1. FIG. 3 illustrates a sectional view of indicator 105, and FIG. 4 illustrates a side view of indicator 105. Indicator 105 includes a base 205, a pair of dials 210 independently rotationally coupled to base 205 using a coupler 215. As seen in FIG. 3, coupler 215 includes a first half $215_1$, and a second half $215_2$ that are coupled together from opposing sides of base 205 to rotationally attach dials 210. Indicator 105 includes a ring 220 or engaging device to be used with elastomeric loop 115 or the like including silicon loops or other materials. In some implementations, non-loop solutions may be used.

FIG. 5 illustrates a front view of base 205 and FIG. 6 illustrates a side view of base 205. Base 205 is a generally circular plate having a central channel 505 with a keying "D" slot. Base 205 also supports ring 220. Base 205 is preferably molded and includes ring 220 and central channel 505. Additionally, each side of base 205 may include suitable molded-in indicia or other visual element that helps to differentiate a category of product for indicator 105 and/or present the appropriate metric element used in cooperation with dial 210. A periphery of base 205 may be scalloped or otherwise patterned for visual effect and/or for assisting a user in gripping indicator 105 such as when rotating a dial 210.

Figure 8:
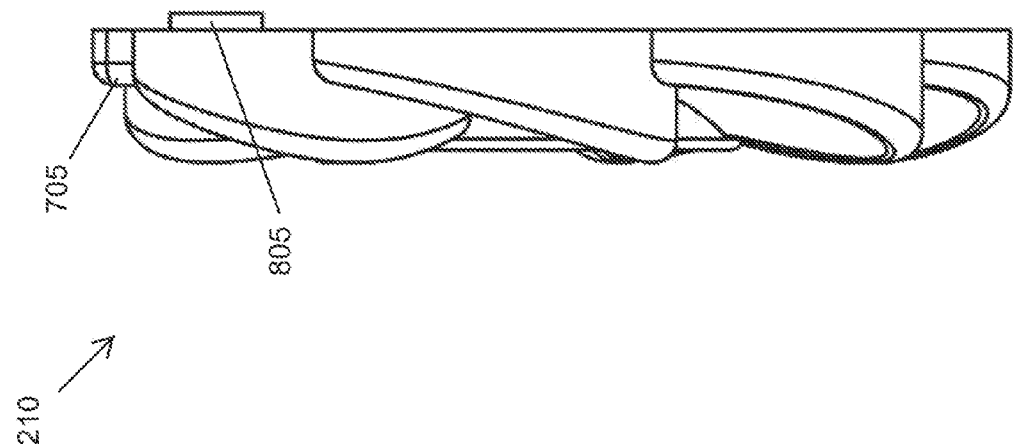
Figure 7:
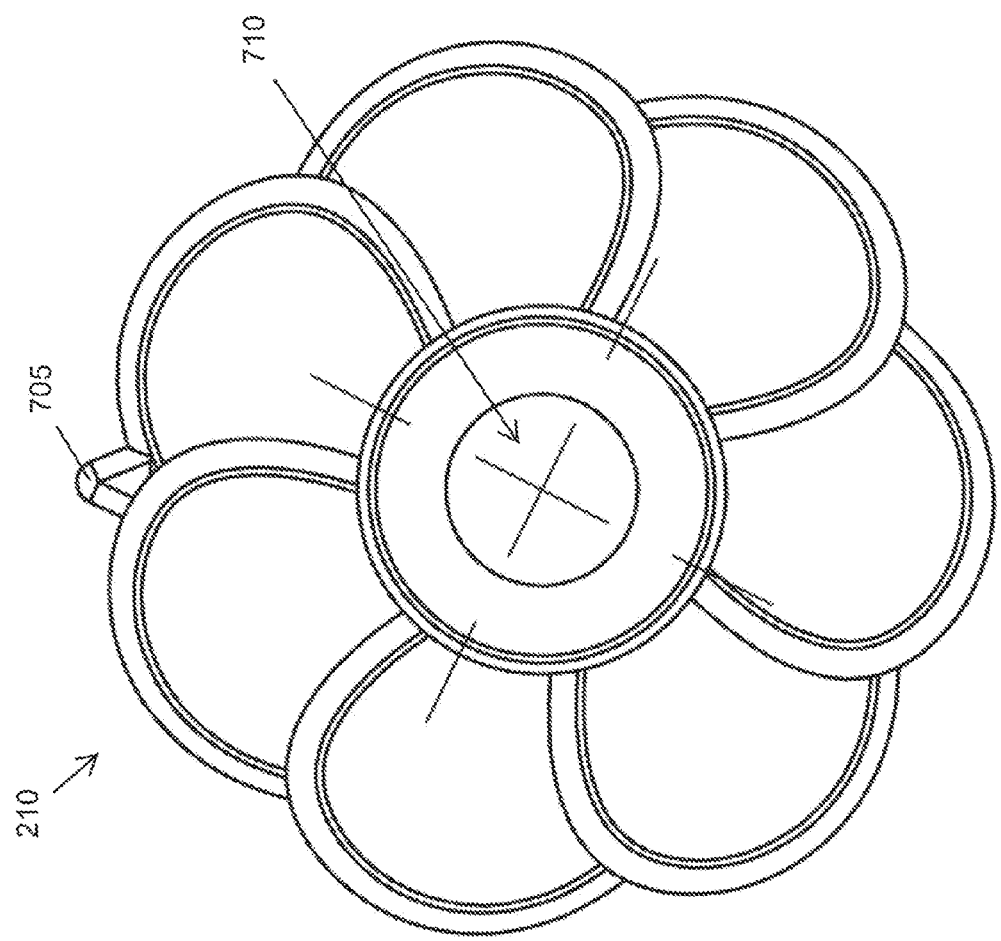

FIG. 7 illustrates a front view of dial 210 for indicator 105 and FIG. 8 illustrates a side view of dial 210. Dial 210 is generally circular and has a smaller diameter than base 205. Dial 210 includes a dial pointer 705 at one location on its periphery, and an optional friction pad 805 on a backside that is proximate base 205 when dial 210 is affixed. A circular channel 710 allows rotation about coupler 215. A face of dial 210 is preferably contoured to permit a user to rotate dial 210 freely around base 205 to position dial pointer 705 in appropriate relationship to the indicia disposed on the faces of base 205. Optional friction pad 805 resists unintended rotation of dial 210 after the user has rotated dial 210 into a desired position. Pressure of coupler 215 holding the pair of dials 210 together against base 205 applies the desired anti-rotational friction. In a preferred embodiment, central channel 505 includes a raised boss on each side that engages a complementary circular channel on a backside of dial 210.

Figure 10:
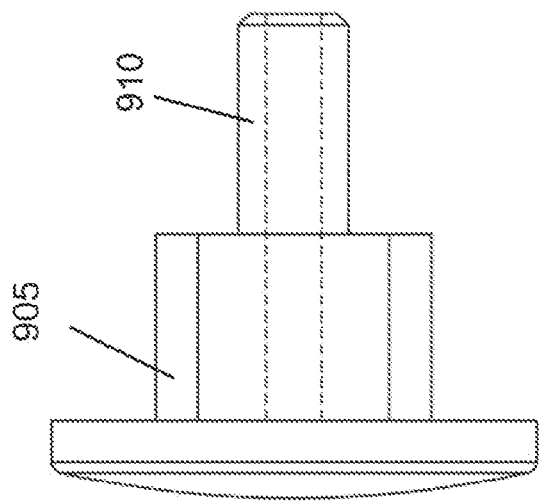
Figure 9:
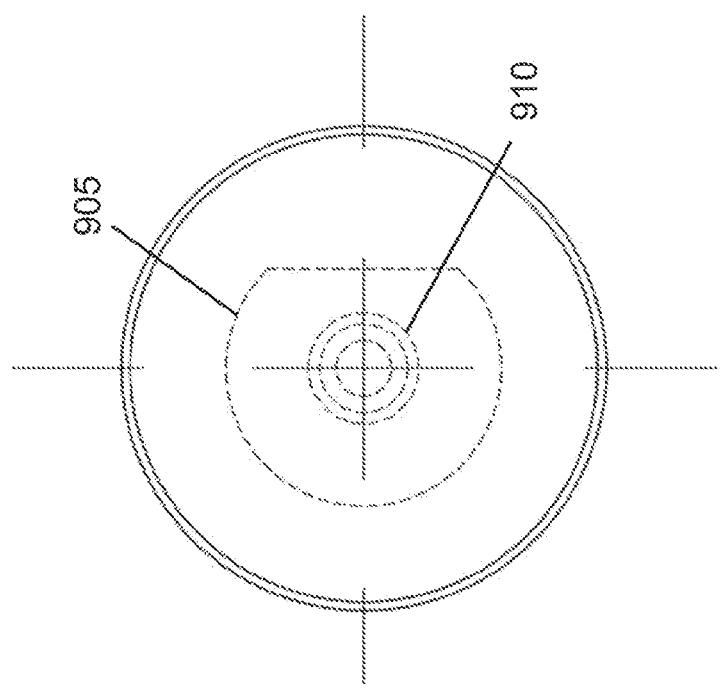

FIG. 9 illustrates a front view of a first half coupler $215_1$ of coupler 215 for indicator 105 and FIG. 10 illustrates a side view of first half coupler $215_1$ of coupler 215. First half coupler $215_1$ includes a body 905 and a shaft 910. Body 905 includes a complementary profile to both central channel 505 and circular channel 710. This ensures that body 905 does not rotate with respect to base 205 in response to rotation of dial 210 about body 905 on one side of base 205, and therefore rotation is not induced into dial 210 disposed on the opposing side of base 205. Shaft 910 is used for mating to second half coupler $215_2$ through central channel 505.

Figure 11:
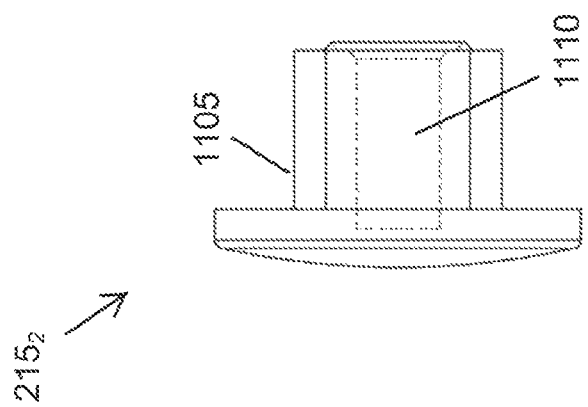
Figure 12:
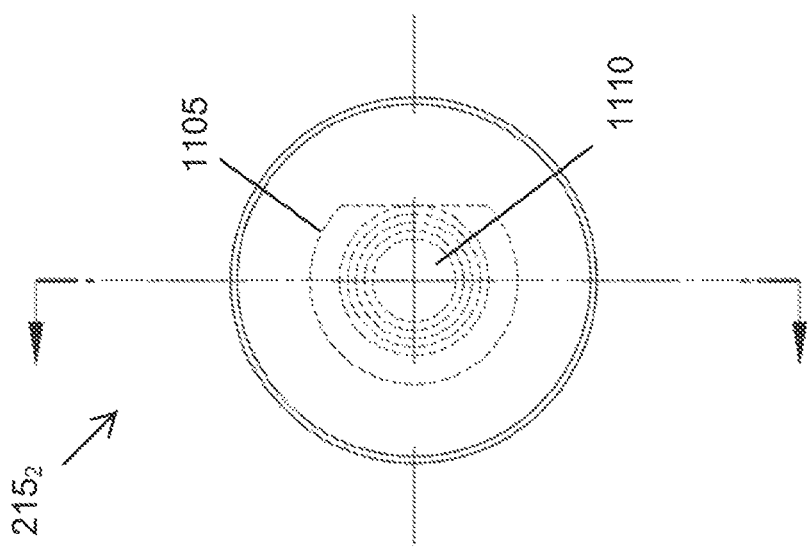
Figure 13:
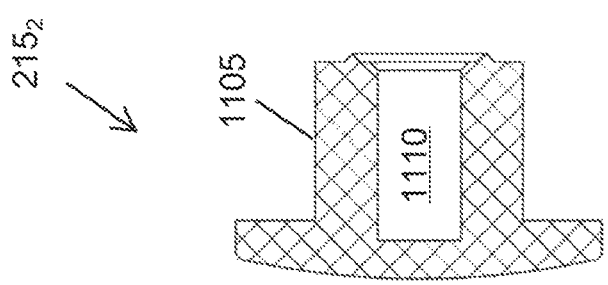

FIG. 11 illustrates a side view of a second half coupler $215_2$ of coupler 215 for indicator 105, FIG. 12 illustrates a front view for second half coupler $215_2$, and FIG. 13 illustrates a sectional view of second half coupler $215_2$. Second half coupler $215_2$ includes a body 1105 defining a cavity 1110 for mating to first half coupler $215_1$. Shaft 910 extends through base 205 and into cavity 1110 to secure the two coupler halves together and form coupler 215.

Components of indicator 105 are preferably injection molded plastic, such as polypropylene, ABS or the like, though other materials are included within the scope of the present invention. First half coupler $215_1$ and second half coupler $215_2$ are preferably ultrasonically welded, though other attachment mechanisms are included within the scope of the present invention, such as snapping interconnection, press/glue, and/or threaded interconnection, or the like.

As noted herein, preferred embodiments for the present invention includes use of indicator 105 in a freshness system 100 directed to differentiating and timing different infant fluid nutrition products disposed in a collection of storage bottles 110, such as in a refrigerator. The infant fluid nutrition product include breast milk and formula, though other categories and products may be addressed by suitably modified embodiments.

In the preferred embodiment, dials 210 have different schemes (e.g., color schemes), though other differentiating attributes may be used as noted herein. Dial 210 associated with breast milk (a breast milk dial) has one color scheme and dial 210 associated with formula (a formula dial) has a second, easily differentiated, color scheme. The side of base 205 revealed by the breast milk dial includes day indicia, the breast milk dial rotated so that dial pointer 705 points to the correct day. The side of base 205 revealed by the formula dial includes hour indicia (preferably 24 hours for indicating both day and night by a 24 hour clock or different indicia for day and night to distinguish 11 AM from 11 PM). The formula dial is rotated to that dial pointer 705 points to the correct hour. In both cases, once dial pointer 705 points to the correct indicia on the correct side of indicator 105, indicator 105 is suspended on the outside of storage bottle 110 with the correct dial 210 (and differentiating scheme) facing outward.

Some implementations may desire different indicia, and indicator 105 may be adapted accordingly. For example, for breast milk some caregivers may prefer an hour indication in addition to, or in lieu of a day indication. In some implementations, there may be stacked or concentric dials for fine-tuning desired time intervals. Alternative systems are used to associate indicator 105 with storage bottle 110 other than the loop.

The alternative freshness system described below includes manufacturability and operational modifications to the first freshness system described above. A general summary of differences include a modification to the connector elements of the center which are two identical pieces that are snapped together (i.e., in contrast to a male/female assembly). Additionally, an outward face of these identical connector elements are optionally flat and identify a location for placement of a sticker (preferably a selectively attachable/removable system that includes tacky/releasable adhesive and the like), decal, indicia, or the like having an identifier (e.g., a number, letter, barcode, or similar). The identifier provides a reference for an application supported by a mobile operating system (OS) device including iOS, Android, Windows 8 and the like. The application will keep track of a person's milk stock with timers corresponding to the day/time as indicated by the freshness system hanging on the bottle. The reference on the connector will correspond to the timer in the application and may optionally include a unique identifier for each bottle to distinguish bottles having similar expiration indicia. An additional optional modification represented in the alternative freshness system is use of positive detents for pointer rotation control. This may be implemented in many ways. The alternative freshness system highlights an embodiment in which an obverse side and a reverse side of an indicator are not coded (e.g., by use of color or other visually distinguishing characteristic) to represent different foodstuffs. That is, in the first freshness system, the sides were distinguishable and a user could associate the visual characteristic of the obverse with breast milk while associating the visual characteristic of the reverse with formula. In some implementations, the two sides had different timing scales appropriate for such different associations. The alternative freshness system does not provide different color coding for the different sides, some embodiments still provide for different time scales (e.g., a "day" scale and an "hour" scale). A user may still associate an indicator having different time scales on the two sides with different foodstuffs. The user also may use the different scales for the same foodstuff in different storage modes. That is the time side could for breast milk that is left out on the counter (which is only good for a matter of hours at that point, not days) and the day scale used when the breast milk is refrigerated.

Figure 14:
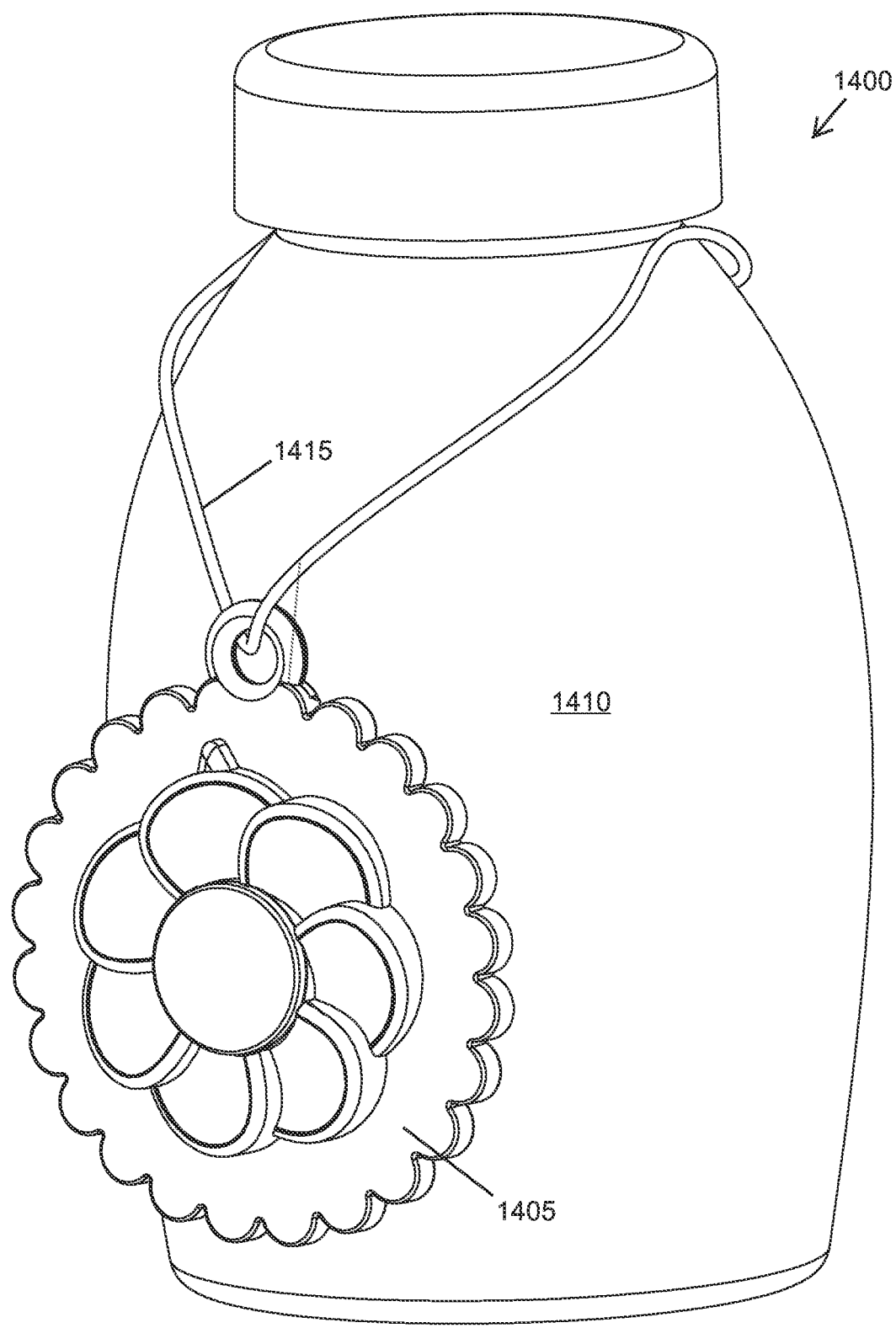

FIG. 14 illustrates a perspective view of an alternative freshness system 1400 including an indicator 1405 disposed on a storage bottle 1410. Indicator 1405 enables a caregiver to identify freshness of a foodstuff (e.g., when a volume breast milk was pumped/expires when storage bottle 1410 includes breast milk or to identify when a certain amount of formula was prepared/expires when storage bottle 1410 includes formula). Indicator 1405 is two-sided, each side including a different time scale to provide a freshness reference associated with and appropriate for the infant fluid nutrition and storage modality (e.g., refrigerated or not) that may be contained within storage bottle 1410. In the preferred embodiment, it is advantageous that a caregiver be able to quickly determine, by reviewing the obverse of indicator 1405 when the fluid nutrition's freshness is going to expire.

Each side of indicator 1405 includes a dial that is used to indicate freshness for the infant fluid nutrition contained within. These dials are independently operable and changing one dial on one side does not change the other dial on the other side. The specific freshness indication of each dial is configured to collectively provide caregivers for appropriate timing options for different fluid nutrition expiration, such as may be based upon storage modality. For example, a refrigerated storage modality may offer acceptable freshness measured in days and a non-refrigerated storage modality may offer acceptable freshness measured in hours. Therefore for this implementation, one side of indicator 1405 associated refrigeration has day indicia disposed thereon. An opposing side of indicator 1405 associated with non-refrigeration has hour indicia disposed thereon. The caregiver is thus easily to use indicator 1405 to using the appropriate freshness metric for the specific category. By using a universal attachment system, e.g., an elastomeric loop 1415 coupled to indicator 1405, indicator 1405 may be used with virtually any size, style, or other configuration of fluid delivery system.

Figure 15:
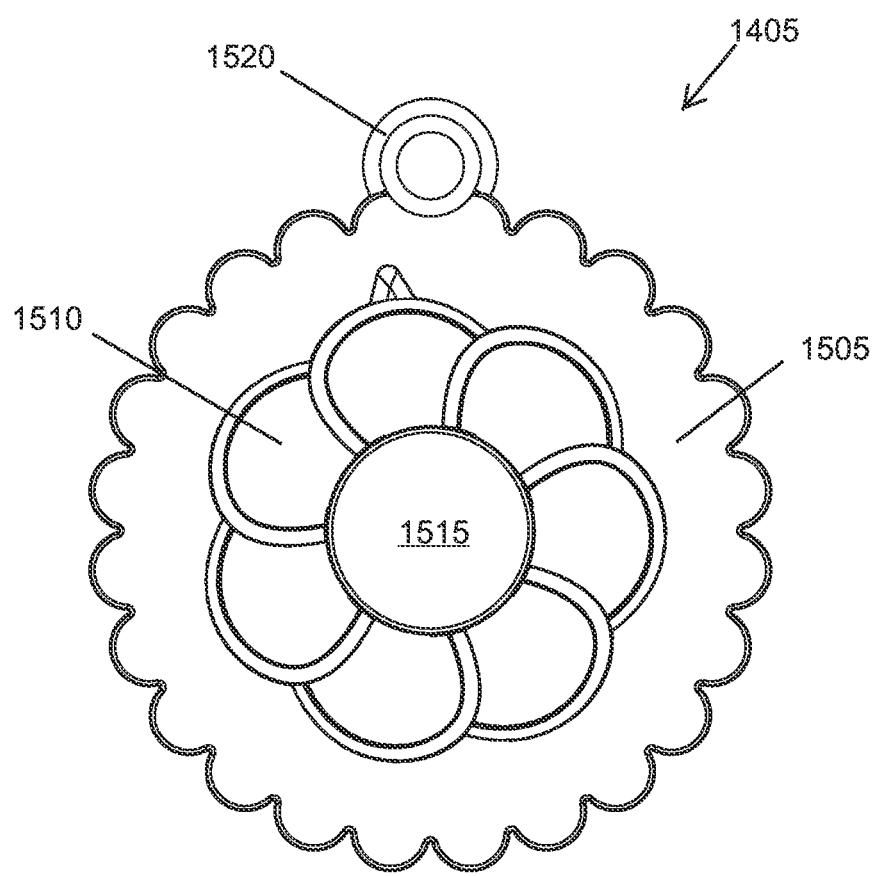
Figure 16:
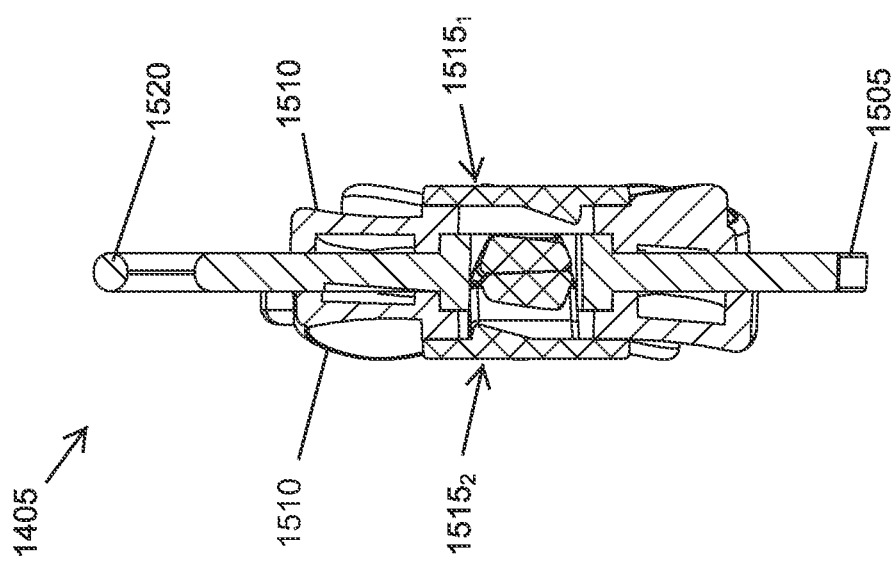
Figure 17:
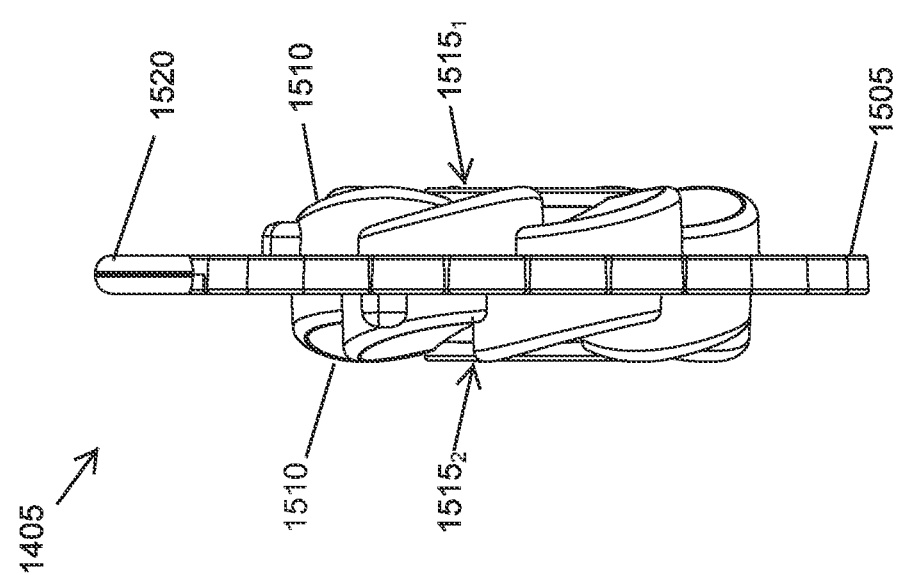

FIG. 15 illustrates a front plan view of indicator 1405 shown in FIG. 14. FIG. 16 illustrates a side sectional view of indicator 1405, and FIG. 17 illustrates a side view of indicator 1405. Indicator 1405 includes a base 1505, a pair of dials 1510 (only one on obverse of base 1505 shown in FIG. 15, the other on an opposite side) independently rotationally coupled to base 1505 using a coupler 1515. As seen in FIG. 16, coupler 1515 includes identical halves that join together (e.g., "snap" together) that simultaneously join dials 1510 to base 1505 and allow independent rotation of each dial relative to the base. Coupler 1515 includes a first half $1515_1$, and a second half $1515_2$ that are coupled together from opposing sides of base 1505 to rotationally attach dials 1510. Coupler halves each provide a planar outside facing portion after being joined together. Indicator 1405 includes a ring 1520 or engaging device to be used with elastomeric loop 1415 or the like including silicon loops or other materials. In some implementations, non-loop solutions may be used.

FIG. 18 illustrates a front view of base 1505 and FIG. 19 illustrates a side view of base 1505. Base 1505 is a generally circular plate having a central channel 1805 with a keying "oval" slot. Base 1505 also supports ring 1520 and a plurality of detent structures 1810 (e.g., recesses within base 1505) disposed 360° around central channel 1805. Base 1505 is preferably molded and includes ring 1520 and central channel 1805. Additionally, each side of base 1505 may include suitable molded-in indicia or other visual element that helps to provide a time scale and/or present the appropriate metric element for indicator 1405 used in cooperation with dial 1510. A periphery of base 1505 may be scalloped or otherwise patterned for visual effect and/or for assisting a user in gripping indicator 1405 such as when rotating a dial 1510.

Figure 21:
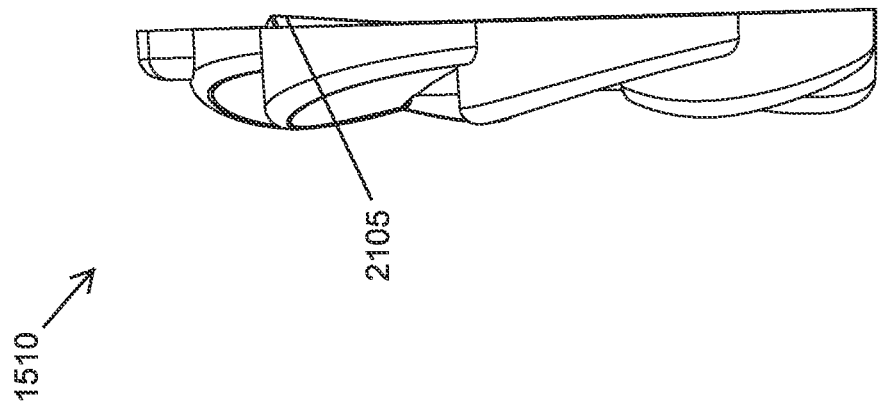
Figure 20:
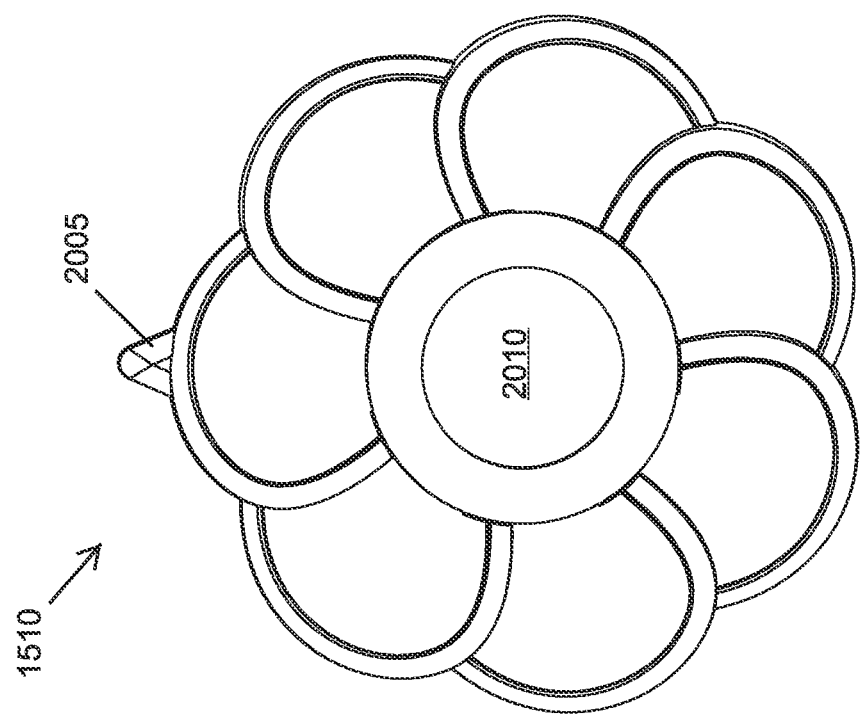

FIG. 20 illustrates a front view of dial 1510 for indicator 1405 and FIG. 21 illustrates a side view of dial 1510. Dial 1510 is generally circular and has a smaller diameter than base 1505. Dial 1510 includes a dial pointer 2005 at one location on its periphery, and detent engagement structure 2105 on a backside that engages base 1505 when dial 1510 is affixed. A circular channel 2010 allows rotation about coupler 1515. A face of dial 1510 is preferably contoured to permit a user to rotate dial 1510 freely around base 1505 to position dial pointer 2005 in appropriate relationship to the indicia disposed on the faces of base 1505. Detent engagement structure 2105 resists unintended rotation of dial 1510 after the user has rotated dial 1510 into a desired position. Engagement of detent engagement structure 2105 with a particular one detent structure 1810 applies the desired anti-rotational control. In a preferred embodiment, central channel 1805 includes a raised boss on each side that engages a complementary circular channel on a backside of dial 1510.

Figure 22:
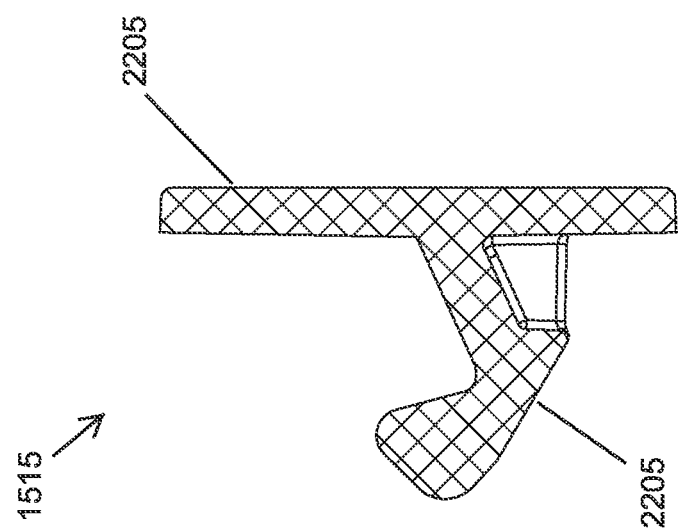
Figure 23:
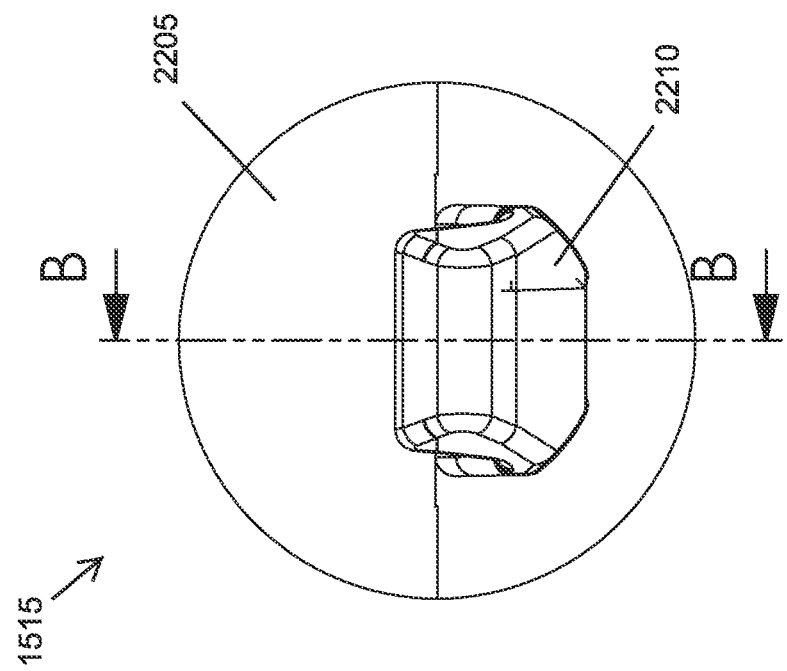

FIG. 22 illustrates a back view of first half of coupler $1515_1$ of coupler 1515 for indicator 1405 and FIG. 23 illustrates a sectional side view of first half of coupler $1515_1$ taken through section B. Each half coupler 1515, includes a body 2205 and a springing locking tab 2210. Springing locking tabs 2210 engage each other through both central channel 1805 and circular channel 2010 and are keyed on the straight edges of the oval slot of central channel 1805. This ensures that body 2205 does not rotate with respect to base 1505 in response to rotation of dial 1510 about body 2205 on one side of base 1505, and therefore rotation is not induced into dial 1510 disposed on the opposing side of base 1505. Base 1505 and both dials 1510 are captured between the pair of opposing bodies 2205.

Components of indicator 105 are preferably injection molded plastic, such as polypropylene, ABS or the like, though other materials are included within the scope of the present invention. First half coupler $1515_1$ and second half coupler $1515_2$ are preferably snap fit together, though other attachment mechanisms are included within the scope of the present invention, such as ultrasonic welding, press fit/glue, and/or threaded interconnection, or the like.

As noted herein, preferred embodiments for the present invention includes use of indicator 1405 in a freshness system 1400 directed to timing infant fluid nutrition products disposed in a collection of storage bottles 1410 and placed in a storage location, such as in a refrigerator or on a counter. The infant fluid nutrition products may include breast milk and formula, though other categories and products may be addressed by suitably modified embodiments.

In the preferred embodiment, dials 1510 have different schemes (e.g., time scales), though other differentiating attributes may be used as noted herein. Dial 1510 associated with refrigeration has one scheme and dial 1510 on an opposite side associated with non-refrigeration has a second, scheme. The side of base 1505 revealed by the refrigeration scheme may include day indicia, the refrigeration dial rotated so that dial pointer 2005 points to the correct day. The side of base 1505 revealed by the non-refrigeration dial includes hour indicia (preferably 24 hours for indicating both day and night by a 24 hour clock or different indicia for day and night to distinguish 11 AM from 11 PM). The non-refrigeration dial is rotated to that dial pointer 2005 points to the correct hour. In both cases, once dial pointer 2005 points to the correct indicia on the correct side of indicator 1405, indicator 1405 is suspended on the outside of storage bottle 1410 with the correct dial 1510 (and scheme) facing outward and the bottle stored.

Some implementations may desire different indicia, and indicator 1405 may be adapted accordingly. For example, some users may wish to differentiate type of fluid nutrition as shown in FIG. 1-FIG. 13 and for breast milk some caregivers may prefer an hour indication in addition to, or in lieu of a day indication. In some implementations, there may be stacked or concentric dials for fine-tuning desired time intervals. Alternative systems are used to associate indicator 1405 with storage bottle 1410 other than the loop.

Figure 25:
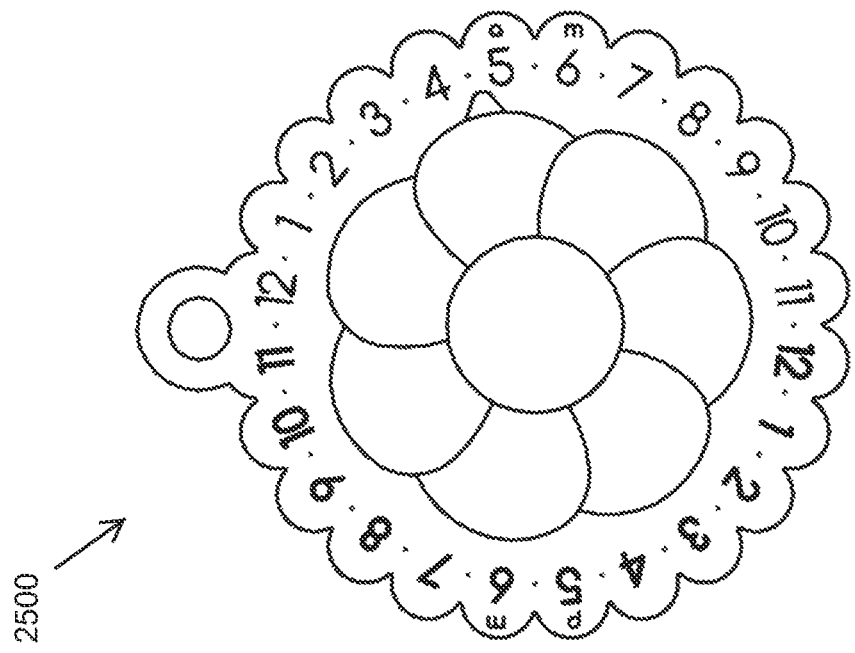
Figure 24:
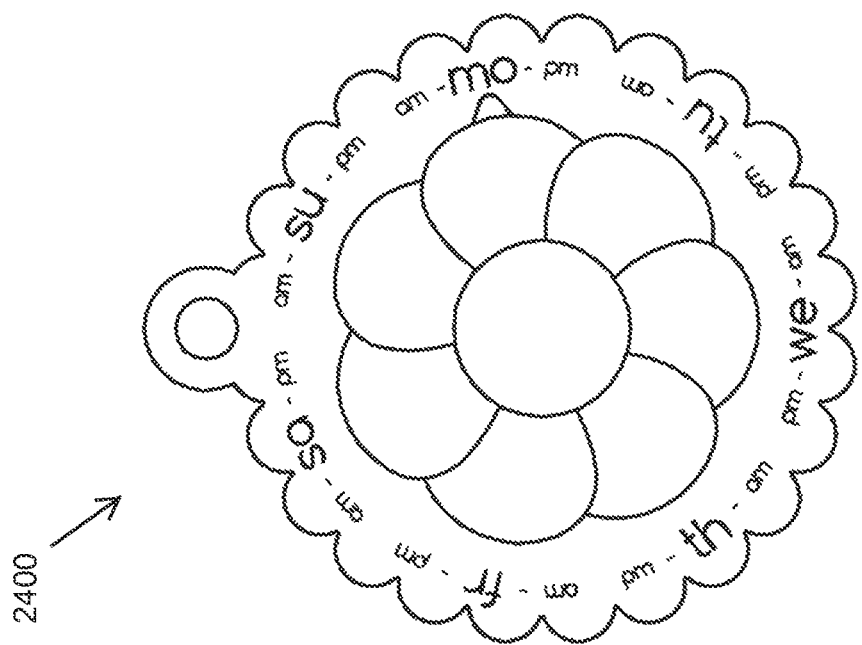

FIG. 24 illustrates a first side 2400 of the indicator shown in FIG. 14 with a first representative freshness scale and FIG. 25 illustrates a second side 2500 of the indicator shown in FIG. 14 with a second representative freshness scale. These are representative freshness scales and other implementations will include different/additional elements or scales. Some users, for example, would associate first side with breast milk and set an expiration day and second side 2500 with formula to set an expiration hour. The user could determine which class of infant nutrition is present by which scale is visible (the opposing side concealed between the visible side and the container). To facilitate this, one side could include some other distinguishing feature to identify the class of infant nutrition. For example, the different color schemes described herein. One or more freshness scales may include both a primary scale (e.g., days or hours) and a secondary scale (half-days, quarter-days, half-hours, quarter-hours, and the like) dependent upon a desired precision in freshness indication.

Figure 26:
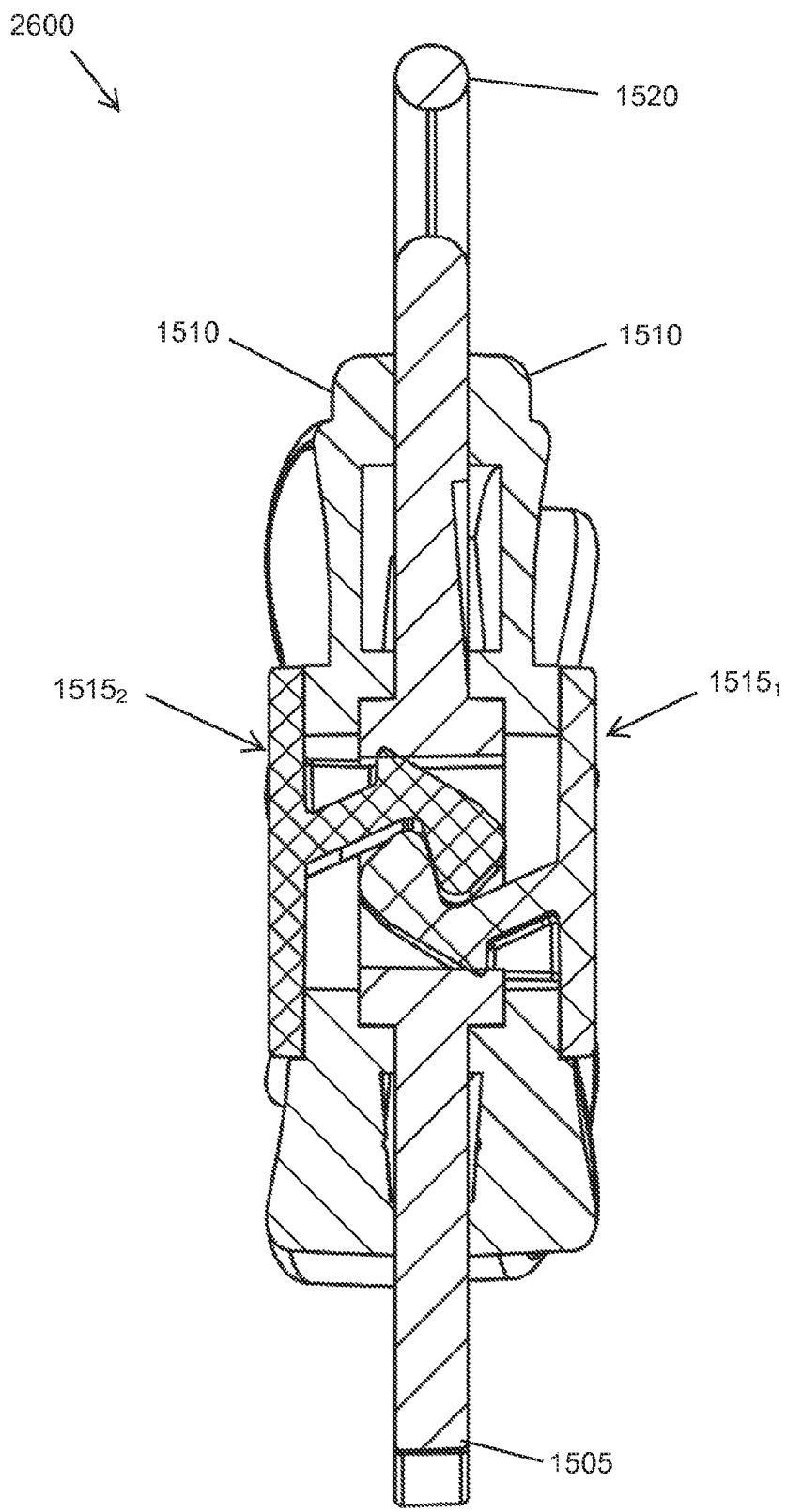

FIG. 26 illustrates a functional sectional view side view 2600 of the indicator shown in FIG. 14. This view in provided to facilitate the understanding of the structures shown in FIG. 16. In FIG. 16, the sectional view does not easily functionally describe the inter-relationships between the dials, plates, and couplers. FIG. 26 provides a better visualization, but it is to be understood that the actual structures are not connected as illustrated in FIG. 26. Side view 2600 includes a rearrangement of the components described in FIG. 16 to aid in understanding how the parts are put together.

In use of these embodiments illustrated in FIG. 14-FIG. 26, a user sets the freshness expiration using the appropriate scale on the appropriate side of indicator 1405. For example, for breast milk that has a relevant reference date (e.g., pumped date or expiration date) on the next upcoming Monday midday, the user sets indicator 1405 as shown in FIG. 24. (When the relevant date to be indicated is in the morning, the user sets indicator 1405 to the "am" label adjacent the appropriate day. Similarly, afternoon relevant dates may be indicated by use of "pm" label adjacent the appropriate day.

The user then uses an elongate flexible loop coupled to ring 1520 to associate indicator 1405 to bottle 1410 with first side 2400 oriented to face outwards from exterior walls of bottle 1410. In this way the user is able to quickly, upon quick visual external examination, establish both that: a) bottle 1410 contains breast milk, and b) the breast milk relevant reference is Monday (e.g., an expiration or a reminder that the breast milk was pumped last Monday allowing the user to quickly calculate the freshness of the breast milk).

The elongate flexible loop may be made of a wide-range of materials. However, embodiments of the present invention include use a loop that is made from a material that provides a high coefficient of friction relative to an outside surface of the container on which it is disposed. These containers typically include glass or plastic construction. When the container includes a neck that widens to form a shoulder transition to a body, then sizing a diameter of the loop to be greater than a diameter of the neck and lesser than a diameter of the body, then concerns regarding a relative coefficient of friction requirement are reduced if not eliminated. However, for containers lacking any appreciable neck or widening transition, then the coefficient is more strongly implicated as the loop is supported on vertical sidewalls of the container by the frictional forces. To facilitate this type of association, embodiments of the present invention provide a mechanism to resize a loop diameter. For example, when the loop is made from thin flexible materials, the loop may be tied in a manner to decrease the loop diameter. Other embodiments may include a slide or other mechanical structure coupled to the loop to variably set a loop diameter.

It is to be noted that the dials of indicator 1405 are independent so the user is able to actually employ both indicators at the same time. A user may set indicator 1405 as described above with MONDAY indicated on the obverse while setting second side 2500 to a particular relevant reference hour on the reverse. This reverse could be used for fine-tuning the scale on the obverse. The user, when reviewing the bottles available for feeding, easily identifies the containers with breast milk and what day the different quantities of breast milk will expire. In the event that the hour information on the reverse side has been set to include valid information, and that information may be valid to discriminate between bottles that each contain breast milk expiring on Monday, the reverse side allows the user to narrow choices further. The elongate flexible loop allows the reverse side and the obverse to be easily flipped so second side 2500 is visible.

In alternative embodiments, the indicators may be configured as a collar that may be placed around a neck of storage bottle. The collar includes appropriate dials/timers and differentiates products based upon which side of the collar was top-most. Similarly, a "coaster" is configured to support a base of a storage bottle, and is otherwise similar to the collar in having differentiating schemes that are selectively visible to indicate different products while indicating an appropriate freshness metric. The present invention further includes simple embodiments having preprinted single or dual-sided freshness indicators that may be appropriately associated with the storage/delivery system. For example, a collection of pendants could be available, each imprinted with a day of the week (e.g., "FRIDAY" or "11 AM"). The appropriate pendant is draped over the neck of the storage bottle.

In other alternatives, the base could be planar and elongate (e.g., a narrow vertical base) with the pointer affixed to independent sliders that move the length of the base to indicate the desired particular indicia of a plurality of indicia of the schemes. Each side has slider that moves separate from the other slider, and each includes a pointer to indicate the freshness metric appropriate to the freshness scheme of the associated side.

The system and methods above has been described in general terms as an aid to understanding details of preferred embodiments of the present invention. In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A freshness system indicating an expiration of a quantity of a fluid nutrition in a container, comprising:
   a planar base having a first side and a second side, said first side including a first freshness scheme and associated first plurality of freshness indicia and said second side including a second freshness scheme and associated second plurality of freshness indicia;
   a first dial rotatably coupled to said first side having a first rotation mode, said first dial including a first pointer and said first rotation mode associating said first pointer with a particular one indicia of said first plurality of indicia;
   a second dial rotatably coupled to said second side having a second rotation mode, said second rotation mode independent from said first rotation mode, said second dial including a second pointer and said second rotation mode associating said second pointer with a particular one indicia of said second plurality of indicia; and
   an attachment system, selectively and removably associating said planar base to the container with a first particular one of said first side or said second side substantially visible while a second particular one of said first side or second side other than said first particular one substantially obscured, wherein said pointer of said particular one side that is substantially visible visibly identifies the expiration of the quantity of the fluid nutrition within the container by reference to the associated particular one indicia of said particular one side.

2. The freshness system of claim 1 wherein said first plurality of indicia includes a number of hours of one day and said second plurality of indicia includes a number of days of one week.

3. The freshness system of claim 2 wherein said number of hours is 24 and wherein said number of days is 7.

4. The freshness system of claim 1 wherein said first scheme includes a first color and said second scheme includes a second color different from said first color.

5. The freshness system of claim 1 wherein said base defines an aperture at a point near an outer edge and wherein said attachment system includes a flexible elongate element engaging said aperture and the container, said attachment system configured to enable either side of said base to be said first particular one side.

6. The freshness system of claim 1 wherein said base and said dials are configured to include a detent system configured to resist rotations of said dials relative to said base.

7. The freshness system of claim 6 wherein said detent system includes a plurality of recesses on each side of said base and wherein each said dial includes a recess-engagement structure selectively engaging one or more of said recesses.

8. The freshness system of claim 1 wherein a coupler rotatably engages each said dial to said base.

9. The freshness system of claim 8 wherein said base and said dials each include a central channel and wherein said coupler includes a pair of couplers engaging each other through said channels when rotatably engaging each said dial to said base.

10. The freshness system of claim 9 wherein said central channel of said base includes an anti-rotation key preventing said coupler from any significant rotation responsive to a first rotation of said first dial which decouples said first rotation of said first dial and inhibits said first rotation from inducing a second rotation in said second dial.

11. A method indicating an expiration of a quantity of a fluid nutrition in a container, comprising:
   a) determining the expiration of the fluid nutrition;
   b) setting one independent pointer of a plurality of independent pointers visually identifying the expiration from a set of candidate expirations associated with each independent pointer as a visually identified expiration, each independent pointer associated with an independent freshness scheme having appropriate associated indicia and each freshness scheme providing a different set of candidate expirations; and
   c) associating removably said one independent pointer to an outside of the container with said one independent pointer and said visually identified expiration visible from a visual examination of said independent pointer without contacting or moving said one independent pointer;
   wherein said plurality of independent pointers includes a first independent pointer on a first side of a base and a second independent pointer on a second side of said base wherein setting said first independent pointer does not alter a freshness indication of said second independent pointer and wherein setting said second independent pointer does not alter a freshness indication of said first independent pointer.

12. The method of claim 11 wherein said one independent pointer is on said first side and wherein said associating step includes removably coupling the base to the container with said first side disposed away from the container and said second side disposed towards the container and located between said first side and the container.

13. A freshness indicating system removably associative with a container of a quantity of an infant nutrition, the quantity of the infant nutrition having an infant nutrition freshness expiration, comprising:
   a customizable variable indicator having a first mode and a second mode, each said mode associated with a different freshness expiration scale having an independently interacting indicator selecting a particular freshness expiration from a set of freshness expirations wherein a selection of said particular freshness expiration in said first mode does not alter a selection of said particular freshness expiration in said second mode and wherein a selection of said particular freshness expiration in said second mode does not alter a selection of said particular freshness expiration in said first mode; and
   an engagement system, coupled to said customizable variable indicator, selectively and repeatably associative with the container presenting a particular one mode of said modes on an exterior of the container configured to permit visual external inspection of said associated freshness expiration scale with said particular one mode including said independently interacting indicator selecting the infant nutrition freshness expiration
   wherein said customizable variable indicator includes a plate having a first side and a second side, a first independently rotating dial indicator disposed on said first side, and a second independently rotating dial indicator disposed on said second side.

14. The freshness indicating system of claim 13 wherein the container includes a bottle and wherein said engagement system includes a ring coupled to said plate and an elongate flexible loop coupled to said ring and configured to secure said plate to said bottle with one of said sides disposed toward said bottle and the other side disposed away from said bottle.

* * * * *